US011571565B2

(12) United States Patent
Capogrosso et al.

(10) Patent No.: US 11,571,565 B2
(45) Date of Patent: Feb. 7, 2023

(54) ELECTRODE ARRAY, A LEAD PADDLE AND A NEUROMODULATION SYSTEM

(71) Applicant: ONWARD MEDICAL N.V., Eindhoven (NL)

(72) Inventors: Marco Capogrosso, Lausanne (CH); Fabien Wagner, Lausanne (CH); Gregoire Courtine, Lausanne (CH); Vincent Delattre, Eindhoven (NL); Karen Minassian, Vienna (AU); Bert Bakker, Eindhoven (NL); Jocelyne Bloch, Paudex (CH); Nathan Greiner, Lausanne (CH); Damien Ganty, Eindhoven (NL); Sjaak Deckers, Eindhoven (NL); Edoardo Paoles, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 69 days.

(21) Appl. No.: 16/426,897

(22) Filed: May 30, 2019

(65) Prior Publication Data

US 2019/0366077 A1    Dec. 5, 2019

(30) Foreign Application Priority Data

May 30, 2018 (EP) .................................. 18175117

(51) Int. Cl.
*A61N 1/05* (2006.01)
(52) U.S. Cl.
CPC ................. *A61N 1/0553* (2013.01)

(58) Field of Classification Search
CPC .......................... A61N 1/0553; A61N 1/36062
(Continued)

(56) References Cited

U.S. PATENT DOCUMENTS

| 6,236,892 B1 * | 5/2001 | Feler ................... A61N 1/0553 607/117 |
| 8,108,051 B2 | 1/2012 | Cross, Jr. et al. |

(Continued)

FOREIGN PATENT DOCUMENTS

| EP | 2243510 A2 | 10/2010 |
| WO | 2014209877 A1 | 12/2014 |

OTHER PUBLICATIONS

Courtine, G. et al., "Transformation of nonfunctional spinal circuits into functional states after the loss of brain input," Nature Neuroscience, vol. 12, No. 10, Oct. 2009, Available Online Sep. 20, 2009, 12 pages.

(Continued)

*Primary Examiner* — Carl H Layno
*Assistant Examiner* — Jane C Kalinock
(74) *Attorney, Agent, or Firm* — Finnegan, Henderson, Farabow, Garrett & Dunner LLP (57) ABSTRACT

The present invention relates to an electrode array for neuromodulation, comprising a first electrode section with more than two electrodes being arranged parallel and densely packed in the first electrode section, further comprising a second electrode section with more electrodes than in the first electrode section, the electrodes in the second electrode section being arranged symmetrically with respect to the longitudinal axis and transversal offset to each other. Furthermore, the present invention relates to a lead paddle and a neuromodulation system.

20 Claims, 4 Drawing Sheets

(58) Field of Classification Search
USPC .................................................. 607/118, 116
See application file for complete search history.

(56) References Cited

U.S. PATENT DOCUMENTS

| | | | |
|---|---|---|---|
| 9,358,384 | B2 | 6/2016 | Dubuclet |
| 10,799,701 | B2* | 10/2020 | Lee .................... A61N 1/36171 |
| 2005/0113878 | A1 | 5/2005 | Gerber |
| 2008/0269854 | A1 | 10/2008 | Hegland et al. |
| 2012/0006793 | A1 | 1/2012 | Swanson |
| 2012/0016453 | A1* | 1/2012 | Feler .................... A61N 1/0553 607/148 |
| 2013/0006793 | A1 | 1/2013 | O'Sullivan et al. |
| 2015/0032187 | A1* | 1/2015 | Ranu .................... A61N 1/0553 607/62 |
| 2019/0344070 | A1* | 11/2019 | Molnar .............. A61B 17/7001 |
| 2019/0381313 | A1* | 12/2019 | Lu ........................ A61N 1/3601 |

OTHER PUBLICATIONS

Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Fyfe, I., "Breakthrough technology restores function after complete paralysis", *Nature Reviews Neurology*, 18(4), 2022, p. 187.

Palmer, Sarah Jane, "Neuromodulation and the life-changing advances in this area of medical technology", *British Journal of Neuroscience Nursing*, Apr./May 2022, vol. 18, No. 2, pp. 70-71.

Rowald, Andreas et al., "Activity-dependent spinal cord neuromodulation rapidly restores trunk and leg motor functions after complete paralysis", *Nature Medicine*, Apr. 2020, htttps://doi.org/10.1038/s41591-021-01663-5, www.nature.com/naturemedicine, 41 pages.

* cited by examiner

ELECTRODE ARRAY, A LEAD PADDLE AND A NEUROMODULATION SYSTEM

CROSS-REFERENCE TO RELATED APPLICATION

The present application claims priority to European Application No. 18175117.3 entitled "AN ELECTRODE ARRAY, A LEAD PADDLE AND A NEUROMODULATION SYSTEM," filed May 30, 2018. The entire contents of the above identified application are hereby incorporated by reference for all purposes.

TECHNICAL FIELD

The present invention relates to an electrode array, a lead paddle and a neuromodulation system.

BACKGROUND AND SUMMARY

Electrode arrays and lead paddles for neuromodulation, especially neurostimulation, are for example known from U.S. Pat. No. 8,108,051 B2, US 2013/0096662 A1, US 2012/0006793 A1 and EP 3 013 411 A1.

For example US 2008/0269854 A1, US 2005/0113878A1 and EP2243510 B1 disclose a device for patient therapy with a specific kind of electrode array, i.e. a lead body suitable for patient implantation; a connection element carried by the lead body and positioned to electrically couple to a pulse generator suitable for patient implantation, and at least three electrical contacts carried by the lead body and positioned relative to the lead body to contact patient tissue and deliver electrical signals to a patient, wherein the spacings between the immediately neighboring contacts of said at least three electrical contacts are at least 8 millimeters.

U.S. Pat. No. 9,358,384 B2 discloses a flexible paddle electrode array which has transverse lines of reduced rigidity or stiffness at these flex or hinge lines, thereby allowing the flexible paddle electrode array to flex or deflect along its length at these hinge lines. Because of the living hinges, the staggered arrangement of the rows of the nonflexible and flexible electrodes, and the flex or hinge lines, the flexible paddle electrode array is able to flex along its length, but to be sufficiently rigid to maintain the nonflexible and flexible electrodes in adequate contact with patient tissue.

It has been found that depending on the implantation site of an electrode array being used and adapted for e.g. spinal cord stimulation, the way of arranging the electrodes influences the neuromodulation, especially the neurostimulation outcome and result.

It is therefore an object of the present invention to provide an electrode array, a lead paddle and a neuromodulation system, which is more adapted and suitable for the stimulation of the spinal cord, the spinal segments and dorsal roots.

This object is solved according to the present invention by a lead paddle positioning and/or deployment system with the features of an electrode array for neuromodulation.

Accordingly, an example electrode array for neuromodulation, comprises: a first electrode section with more than two electrodes being arranged parallel and densely packed in the first electrode section, and further comprising a second electrode section with more electrodes than in the first electrode section, the electrodes in the second electrode section being arranged symmetrically with respect to the longitudinal axis and with a transversal offset to each other.

The invention is based on the basic idea that with the combination of the first and the second electrode section two different means for specifically evoking targeted pools of motor neurons are provided. By means of an increased density of electrodes in the first section of electrodes, e.g. positioned in an application for spinal cord stimulation above the sacral level of the spinal cord in spinal cord stimulation, a current steering possibility may be provided to enhance stimulation specificity. In particular, a so-called electrode belt can be established with the more than two electrodes being arranged parallel and densely packed in the first electrode section. The stimulation with an electrode belt allows a well-defined (current steering) stimulation at the sacral level and can potentially target any desired spinal segment located above ("belt array" strategy). The "standard" regular paddle design configuration in the second electrode section is provided with regularly spaced electrodes for targeting dorsal roots at their entry point in spinal segments.

The electrode array may be configured and adapted for implantation into mammals, in particular human patients.

The electrode array be arranged for Central Nervous System (CNS) Stimulation. In particular, the electrode can be designed for the stimulation of the spinal cord.

It is possible to provide neuromodulation and/or neurostimulation with the electrode array to the CNS. CNS Stimulation can be done by Epidural Electrical Stimulation (EES) (or similarly subdural stimulation, hereinafter always to be understood as possible alternative to EES). Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso, M, et al., A Computational Model for Epidural Electrical Stimulation of Spinal Sensorimotor Circuits, Journal of Neuroscience 4 Dec. 2013, 33 (49) 19326-19340, Courtine et al., Transformation of nonfunctional spinal circuits into functional states after the loss of brain input, Nat Neurosci. 2009 October; 12(10): 1333-1342. Moraud et al, Mechanisms Underlying the Neuromodulation of Spinal Circuits for Correcting Gait and Balance Deficits after Spinal Cord Injury, Neuron Volume 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low, and the imprecisions hinder fluidity and full functionality in the potential space of the movement. For example, neuromodulation and/or neurostimulation of the CNS may be used to enhance and/or restore the capabilities of the patient as regards movement, especially in a way that the existing ways of physiological signal transfer in the patient's body are supported such that the command signals for body movement or the like still are provided by the patient's nervous system and just supported and/or enhanced or translated by the CNS stimulation module.

Furthermore, it is possible that the first electrode section is arranged at a proximal end of the electrode array and/or the second electrode section is arranged at a distal end of the electrode array. The proximal end is especially the end of the electrode array, which is considering the implanted situation or the situation during implantation of the electrode array proximal than the second electrode section, which is then at the distal end or in a more distal position. By arranging the first electrode section close to the proximal end, the belt electrode strategy can be applied close the entry point or channel, where the electrode array and its carrier (e.g. a lead paddle) are positioned at and/or around the spinal cord. A more precise position can be provided with such a design and arrangement.

The electrodes in the first electrode section can be identical. This helps to enhance the effects of the belt array strategy as outlined above. Also, the steering predictability is enhanced as identical electrodes with inter alia identical functionality are used. This increases the predictability of the stimulation capabilities of the electrodes of the first section.

Also, the electrodes in the second electrode section can be identical. Thus, also in the second section the manufacturing is simplified and also the predictability of the stimulation result may be enhanced.

It is possible that electrodes are identical. By providing (only) identical electrodes, the manufacturing process may be simplified. Also, the stimulation behavior becomes more predictable as the electrodes are more comparable to each other when compared with an approach, where different forms of electrodes are used.

The electrodes may have a rectangular stimulation area. The stimulation area shall be understood as the area, which is effectively participating in the stimulation, i.e. the area which can be effectively used to send out stimulation signals and/or receive stimulation signals or other signals.

At least one electrode may have a length that is 2.0-4.0 times of the width. This relationship was found to be beneficial in trials as by this form stiffness in axial direction (i.e. along the longitudinal axis) of the electrode array and its carrier can be enhanced. Especially, the length may be 2.5-3.0 times of the width. An example value for the length could be chosen at around 2.6-2.7 times of the width.

Example dimensions of an electrode, especially of an electrode with rectangular form, can be approx. 4.0-6.0 mm length and approx. 1.3-2.5 mm width.

All electrodes may have the same orientation. Especially, it is possible that all electrodes have an orientation parallel to the longitudinal axis of the electrode array. In case that the electrodes have a form with a longer extension in one direction than the other, e.g. oval form, rectangular form or the like, and by arranging the electrodes all in the same direction, the stiffness and flexibility of the array of electrodes and its carrier can be influenced. If, for example, all electrodes have a form with a longer extension along their longitudinal axis and are oriented all in the same direction of the longitudinal axis, then the stiffness in the longitudinal direction is increased, while in radial direction still more flexibility and elasticity is offered. Such a design is especially beneficial for electrode arrays to be placed in the spinal channel for spinal cord stimulation.

The electrode array may have a length that is of 8-14 times of the length of an electrode, especially approximately 12 times of the length of an electrode. For example, if the length is chosen in a range of 4.00-6.00 mm, then the length of the array may be for example within a range of 50-70 mm. A suitable width of the electrode may then be chosen in a range of 10-13 mm. With such dimensions, sufficient area and volume of the spinal cord may be stimulated. Several segments of the spine and the respective parts of the spinal cord may be covered and stimulated this way.

The first electrode section and the second electrode section can be for example separated by a gap that is larger than the length of an electrode, especially wherein the length of the gap is chosen in a range of approx. 100-160% of the length of an electrode. A possible setup may be chosen such that the length of the gap is chosen in a range of approx. 100%. These dimensions have been found to be beneficial based on the following observations and consideration: The radiation and stimulation sent out from an electrode can also reach and stimulate areas adjacent to the electrode. Thus, also electrodes can be arranged spaced apart from each other without losing possible coverage of the area/volume to be stimulated. By choosing the gap in a range of approx. 130-160% of the length of an electrode still sufficient coverage of the area/volume to be stimulated can be reached. Also, it is possible to increase the overall length of the electrode in the longitudinal direction, which is beneficial especially in the field of spinal cord stimulation. So, a longer segment of the spinal cord can be covered and stimulated with the electrode array.

The electrode array can for example comprise a longitudinal axis in the direction of the longitudinal orientation of the electrodes, wherein the first electrode section is symmetrical with respect to the longitudinal axis and with respect to a radial axis in the first electrode section perpendicular to the longitudinal axis. Symmetry in this section helps to increase the steering capabilities and the electrode belt stimulation strategy.

Alternatively and/or additionally it is possible that the second electrode section is symmetrical with respect to the longitudinal axis and asymmetrical with respect to a radial axis in the second electrode section perpendicular to the longitudinal axis. Asymmetry is the second electrode section is helpful to achieve greater coverage of area/volume to be stimulated with the electrodes arranged in the second electrode section.

Although the second electrode section may be in that asymmetrical, the pattern of the electrodes in this section may still be a regular one, i.e. that the distance of neighboring electrodes and the arrangement of neighboring electrodes always stays the same (or more or less the same) in the second electrode section.

The first electrode section can comprise at least 3 columns, preferably at least four or five columns, aligned with the longitudinal axis and/or only one radial row along the radial axis. Three or more columns have found to be sufficient to establish successfully an electrode belt array strategy. Preferred setups comprise four or five columns. No further radial row has been found to be necessary.

The second electrode section can comprise for example at least 3 columns aligned with the longitudinal axis and more than 5 radial rows, preferably more than 7 rows, especially at least 8 rows. With such an arrangement, more coverage in longitudinal direction than in radial direction can be provided. This is especially beneficial in spinal cord stimulation, where in the spinal channel it is desirable to stimulate the spinal cord over a substantial part of the spinal cord and over several segments. In other words, one can say the longer the electrode array, the better it is for spinal cord stimulation.

The distance between electrodes of the first section can be for example less than the width of an electrode chosen in the range of approx. 50% to 95% of the width of an electrode, especially approx. 55-75% of the width of an electrode. A possible setup may be chosen such that the width of an electrode chosen in the range of approx. 55% of an electrode. By this, a dense packing of the electrode can be provided. Also, still the steering of the stimulation and the stimulation overlap can be managed very precisely.

Furthermore, for example in the second electrode section the electrodes in neighboring columns can be arranged to each other with a transversal offset. With such a transversal offset a good stimulation area coverage can be established. Also, in this way more coverage in for example the longitudinal direction with some coverage in radial direction can be provided with less electrodes.

Furthermore, in the second electrode section the distance between neighboring electrodes (or distance between neighboring contacts/electrodes or the distance to the neighboring contact/electrode) arranged in the same column can be for example chosen in the range of 135% to 155% of the length of an electrode, especially in the range of 140% to 150% of the length of an electrode.

Moreover, additionally and/or alternatively in the second electrode section the distance between neighboring rows can be chosen in the range of 130% to 150% of the width of an electrode, especially in the range of 135% to 145% of the width of an electrode.

These ranges have been found to be beneficial to achieve the aim of providing sufficient stimulation coverage in for example the longitudinal direction with some coverage in radial direction with less electrodes.

For example, the electrode array may comprise a number of electrodes chosen in the range of 8-32 electrodes, preferably 14-18 electrodes, most preferably 16 electrodes. It has been found that a number of electrodes chosen in the range of 10-20 electrodes allows sufficient precise stimulation and at the same time is good to handle in terms of complexity of the electronic system. The range of 14-18 electrodes has been found to be advantageous, as in this range steering and precise stimulation is possible. 16 electrodes appear to be the best compromise in steering capabilities, preciseness of the stimulation to be provided and also the area/volume to be stimulated and at the same time still manageable complexity of the necessary electronic system for the electrodes, by at the same time reducing side effect. The effects have been observed during trials (animal tests and clinical trials), which have not yet been published.

Furthermore, the present invention relates to a lead paddle comprising at least one electrode array as defined above.

The lead paddle may be a lead paddle of a neuromodulation system, especially of a neurostimulation system.

Also, the present invention relates to a neuromodulation system comprising at least one electrode array as defined above and/or at least one lead paddle as defined above.

The neuromodulation system can be for example a neurostimulation system, especially a neurostimulation system for the stimulation of the spinal cord. In particular, the neurostimulation system may be a system to provide inter alia, but not limited to, EES. It can be a combined system that can provide EES and FES for example.

BRIEF DESCRIPTION OF THE FIGURES

Further details and advantages of the present invention shall now be disclosed in connection with the drawings.

It is shown in

It will be appreciated that FIGS. 1-5 show example configurations with relative positioning of the various components. Further, the components are shown to scale. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

DETAILED DESCRIPTION

Figure 1:
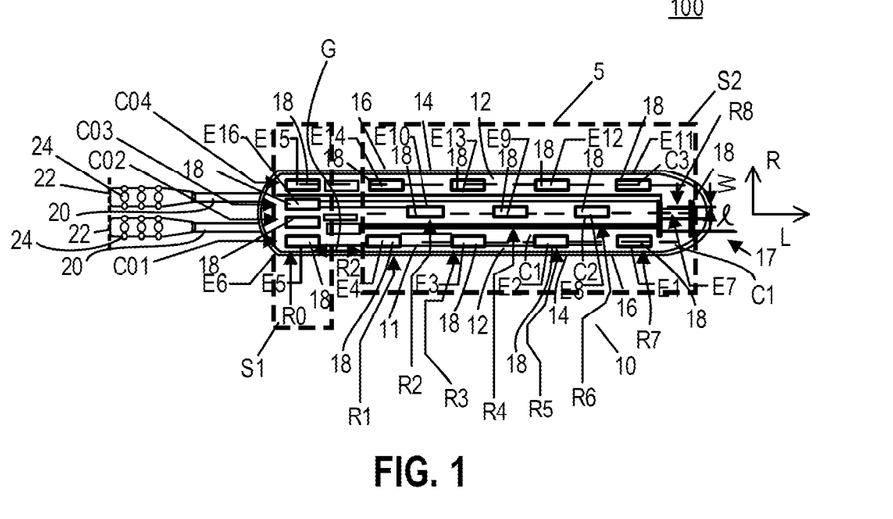
FIG. 1 a view from above of a possible embodiment of an electrode array according to the present invention for a lead paddle and a neuromodulation system according to the present invention.

FIG. 1 shows a view from above of a possible embodiment of an electrode array 5 according to the present invention for a lead paddle 10 and a neuromodulation system 100 according to the present invention.

For better orientation in FIG. 1, a longitudinal axis shall be understood as being aligned (i.e. identical or parallel to) the longitudinal direction L.

A radial axis shall be understood as being aligned (i.e. identical or parallel to) the radial direction R.

The lead paddle 10 comprises a lead paddle body 11 and comprises two guiding channels 12.

The two guiding channels 12 are embedded in the lead paddle body 11.

The lead paddle body 11 may be made of a medical grade material, such as a medical grade polymer. In particular, a medical grade silicone or the like may be used.

The guiding channels 12 extend over more than half of the length of the length of the lead paddle 10.

Especially, the guiding channels 12 extend over more than a half, for example, 80% of the length of the lead paddle 10.

In particular, the guiding channels 12 are arranged along the outer edge region 14 of the lead paddle 10.

In particular, the guiding channels 12 are arranged parallel to the longitudinal edge 16 of the lead paddle 10.

The lead paddle 10 comprises a plurality of electrodes 18 forming the electrode array 5.

Here, in the shown embodiment 16 electrodes 18 are provided.

The electrodes 18 are embedded in the body of the lead paddle 10.

Each specific electrode 18 has a respective denotation "E", in combination with a number "n", with "n" being an integer between 1 to 16.

The shape of the electrodes 18 is rectangular.

All electrodes 18 have the identical form. The shape of all electrodes is more or less identical. Here the electrodes 18 are all identical in their form.

The electrodes 18 have a length l that is 2.0-4.0 times of the width w, especially 2.5-3.0 times of the width. Here they have a length that is approx. 2.6 times of the width to form an elongate shaped rectangular electrode form.

Generally speaking, the form of one or more electrodes can be designed differently. In particular, they can be oval, round, square, diamond shape, trapezoidal or the like.

The electrodes 18 form the electrode array 5 for neurostimulation.

The electrode array 5 has a length that is of 8-14 times of the length of an electrode, here in the shown embodiment approximately 12 times of the length of an electrode 18.

All electrodes 18 have the same orientation. In particular, all electrodes 18 have an orientation parallel to the longitudinal axis of the electrode array 5.

The electrode array 5 comprises a first electrode section S1 with four electrodes 18.

The electrodes 18, here the electrodes E5, E6, E15 and E16 of the first electrode section S1 are arranged parallel and densely packed in the first electrode section S1.

The first electrode section S1 is arranged at the proximal end P of the lead paddle 10.

The first electrode section S1 comprises here four columns C01, C02, C03, C04 aligned with the longitudinal axis and only one radial row R0 along the radial axis in this first electrode section S1.

The distance between electrodes 18 of the first electrode section S1 is less than the width w of an electrode 18 chosen in the range of approx. 50% to 95% of the width of an electrode 18 and here chosen at approx. 55-75% of the width of an electrode 18.

A second electrode section S2 is arranged at the distal end D, i.e. the section orientated to the tip end 17 of the lead paddle 10.

The first electrode section S1 and the second electrode section S2 are separated by a gap G that is larger than the length l of an electrode 18.

Here, the length l2 of the gap G is chosen in a range of approx. 100-150% of the length of an electrode 18.

In the second electrode section S2 more electrodes 18 than in the first electrode section S1 are provided, i.e. electrodes E1-E4, E7-E10 and E11-E14.

The electrodes 18 in the second electrode section S2 are arranged symmetrically with respect to the longitudinal direction L and with transversal offset to each other.

The second electrode section S2 comprises at least three columns C1, C2, C3 aligned with the longitudinal axis and eight rows R1, R2, R3, R4, R5, R6, R7, R8.

In the second electrode section S2 the distance between neighboring electrodes 18 arranged in the same column C1, C2, C3 is chosen in the range of 135% to 155% of the length of an electrode 18, here in the range of 140% to 150% of the length l of an electrode 18.

Also, in the second electrode section S2 the distance between neighboring rows R1, R2, R3, R4, R5, R6, R7, R8 is chosen in the range of 130% to 150% of the width w of an electrode 18, here in the range of 145% to 155% of the width w of an electrode 18.

The arrangement of the electrodes 18 is also such that some electrodes are offset to each other.

Here, in the second electrode section S2 the electrodes 18 in neighboring columns C1 to C2 and C2 to C3 are arranged relative to each other with a transversal offset.

So and as clearly can be seen from e.g. FIG. 1, the electrode array 5 comprises a longitudinal axis in the direction of the longitudinal orientation of the electrodes 18, wherein the first electrode section S1 is symmetrical with respect to the longitudinal axis and with respect to a radial axis in the first electrode section S1 perpendicular to the longitudinal axis and the second electrode section S2 is symmetrical with respect to the longitudinal axis and asymmetrical with respect to a radial axis in the second electrode section S2 perpendicular to the longitudinal axis.

The electrodes 18 of the lead paddle 10 are connected to lead bodies 20.

The lead bodies 20 are connected to a connection portion 20a on the upper side 10a of the lead paddle 10.

This connection portion 20a is on the opposite side of the contact side 10b of the lead paddle 10, that is configured and arranged to get in contact with the tissue to be stimulated, i.e. here the spinal cord of the patient.

Furthermore, the connection portion 20a is arranged centric with regard to the axial axis of the lead paddle 10. Moreover, the connection position 20a is positioned with an offset d to the edge of the proximal end 10c of the lead paddle 10.

As the connection portion 20a of the lead bodies 20 is not directly arranged at the outer edge of the lead paddle 10, the deployment and positioning of the lead paddle 10 is enhanced.

In particular, the offset d helps that by means of the lead bodies 20 the lead paddle 10 may be moved back and forth and also to the left and right and vice versa even after deployment in the spinal canal. As the lead bodies are arranged on the upper side with an offset to the edge, the proximal edge of the lead paddle is free and especially a movement in the proximal direction is not obstructed by the lead bodies.

As can be further seen in FIG. 1, the lead bodies 20 can be provided with anchoring sleeves 22.

The anchoring sleeves 22 are attached to the outer side of the lead body 20.

Furthermore, the anchoring sleeves 22 are provided with pins 24 or so-called anchor bumps 24, which extend radially from the outer side of the anchoring sleeve 22.

Figure 2:
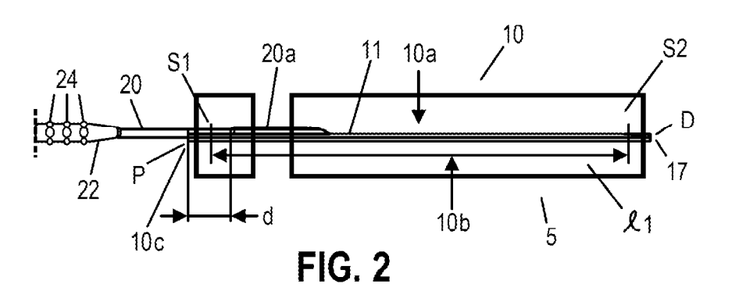
FIG. 2 a side view of the lead paddle and the electrode array according to FIG. 1.

FIG. 2 shows a side view of the lead paddle and the electrode array according to FIG. 1.

As can be seen in FIG. 2, the electrodes 18 protrude out of the surface of the contact side 10b.

Figure 3:
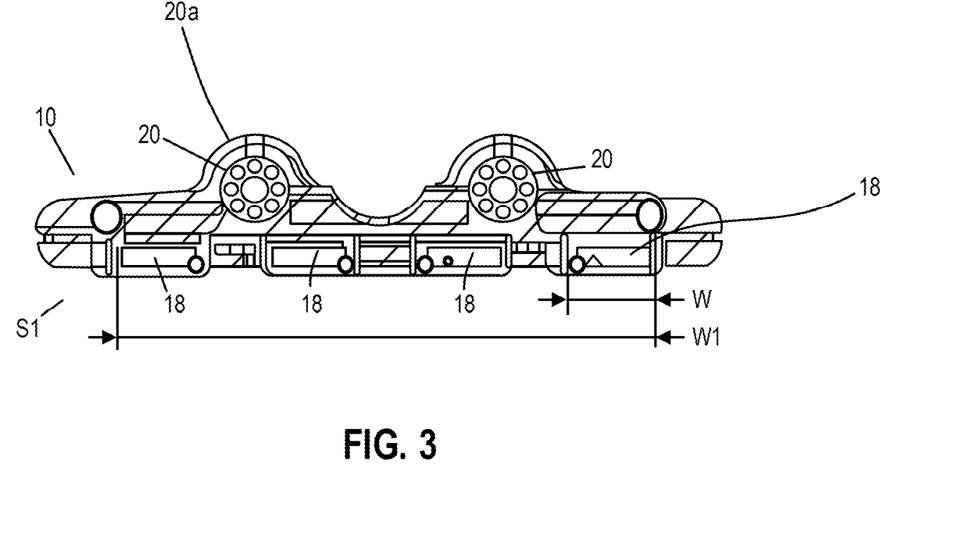
FIG. 3 cutaway drawing through the first section of the lead paddle and the electrode array according to FIG. 1.

FIG. 3 shows cutaway drawing through the first section of the lead paddle and the electrode array according to FIG. 1.

On the upper side 10a the connection portions 20a of the lead bodies 20 can be seen.

Due to the arrangement of the electrodes 18 and the spacing between the electrodes 18, the form of the electrodes 18, the lead paddle body 11 and thus the lead paddle 10 comprises axial stiffness in the longitudinal direction L and radial flexibility in the radial direction R.

So, it is generally possible that even without a stylet and by means of the lead bodies 20 the lead paddle 10 can be inserted into the spinal channel. For such an insertion axial stiffness is necessary to avoid bending in axial direction, whereas (slight) bending in the radial direction is wanted to adapt to the anatomical structures at the implantation site in the spinal channel.

The first electrode section S1 and the second electrode section S2 provide two different means for specifically evoking targeted pools of motor neurons.

Figure 4:
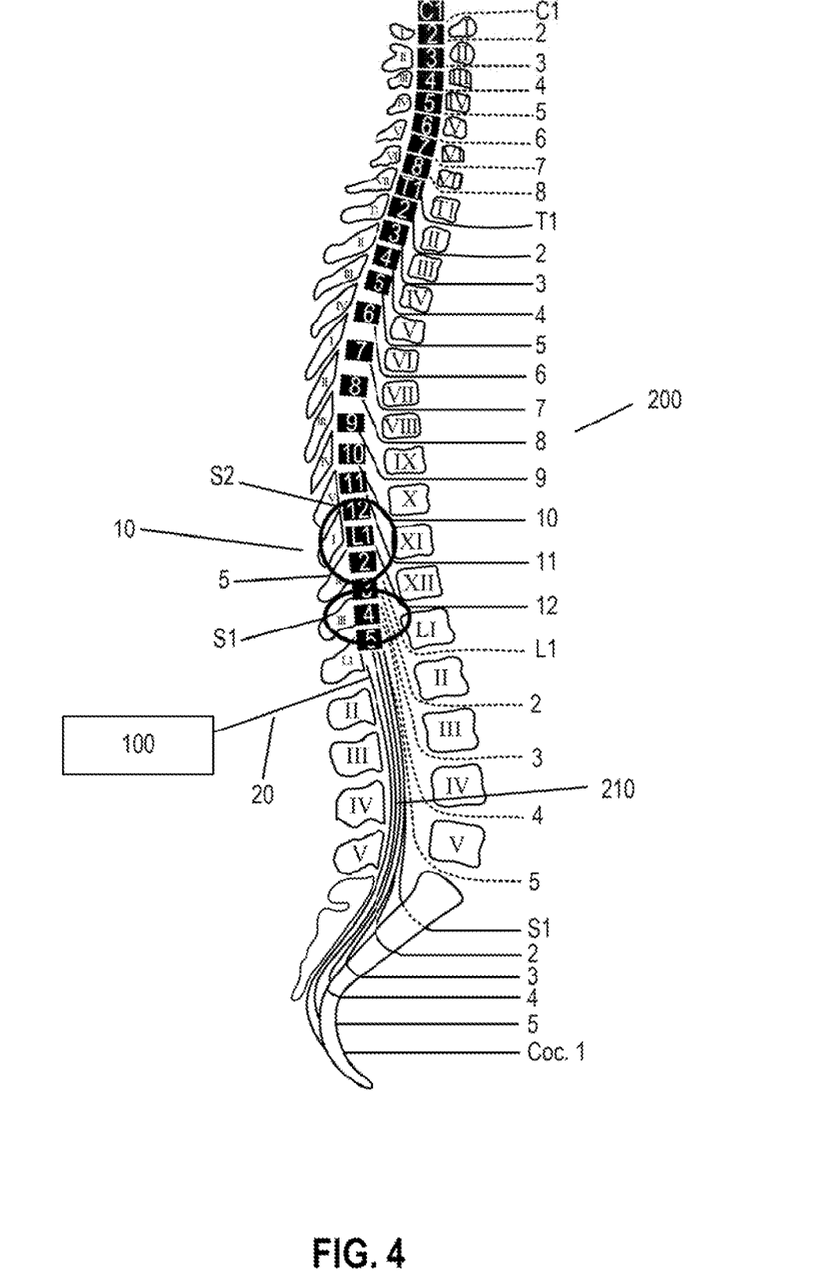
FIG. 4 a schematical drawing of the spinal cord with the embodiment of the lead paddle of FIG. 1.

FIG. 4 shows a schematical drawing of the spinal column 200 and the spinal cord 210 with the embodiment of the lead paddle 10 with the electrode array 5 as described above.

By means of the increased density of electrodes 18 in the first electrode section S1, e.g. positioned in an application for spinal cord stimulation above the sacral level of the spinal cord 210 in spinal cord stimulation as shown in FIG. 4, a current steering possibility may be provided to enhance stimulation specificity. In particular, a so-called electrode belt is established with the four electrodes 18 (i.e. electrodes E5, E6, E15, E16) being arranged parallel and densely packed in the first electrode section S1.

In FIG. 4 it can been seen that dorsal roots enter the spinal cord in their respective segment (i.e. C1 root enters at C1 spinal segment). The exit point of the vertebrate column for lumbo-sacral roots is located rather far apart of their respective entry point in the spinal cord. Especially, lumbar and sacral roots overlay each other like a "spaghetti bag" around the conus medullaris region.

From this anatomical structure and the needs for stimulation of these anatomical structures the following specific points are addressed by the electrode array 5 of the present invention:

The stimulation with an electrode belt allows a well-defined (current steering) stimulation at the sacral level can potentially target any desired spinal segment located above ("belt array" strategy).

The "standard" regular paddle design configuration in the second electrode section S2 is provided with regularly spaced electrodes for targeting dorsal roots at their entry point in spinal segments. This is based on the finding that a regularly spaced electrode array would work well in the cervical area to specifically address individual spinal segments, but that this specificity will deteriorate when sliding the array toward sacral region. Yet, it will still quite sufficient for upper lumbar segments.

Figure 5:
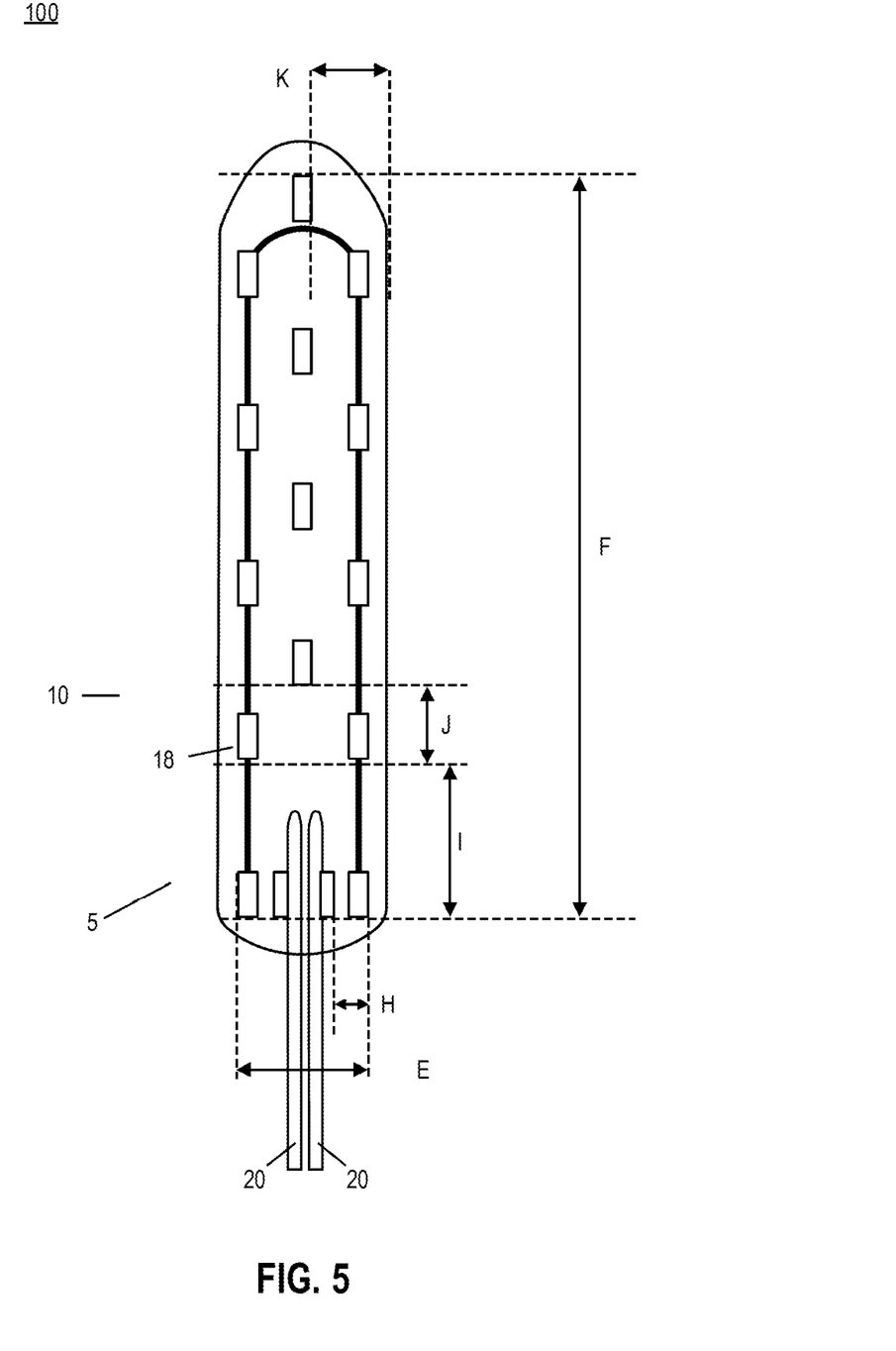
FIG. 5 the lead paddle according to FIG. 1 with further details.

FIG. 5 shows the lead paddle 10 with the electrode array 5 according to FIG. 1 with further details.

In particular, FIG. 5 shows in greater detail the dimensions and the lead paddle 10 with the electrode array 5 with example values for distances.

Inter alia, the
distance E between outermost edges of the electrode array (width) w1 is approx. 11.5 mm,
distance F between outermost edges of the electrode array (length) l1 is approx. 65 mm (cf. also FIG. 2),
distance H between the right outermost edges of two neighboring electrodes 18 is approx. 3.15 mm,
distance I between proximal edge of section S1 is approx. 13.25 mm,
distance J between proximal edge from R1 to R2 is approx. 6.7 mm, and
distance K from longitudinal right edge of electrode in C2 to right outer longitudinal edge of the lead paddle 10 is approx. 6 mm.

The overall dimensions/size of one electrode 18 is approx. 2×5.5 mm with 0.25 mm. In the shown embodiment, a minimum exposed electrode surface to tissue of at least 10 $mm^2$ was required and is reached with this setup, as the exposed electrode surface of an electrode 18 is approx. 11 $mm^2$.

REFERENCES

| | |
|---|---|
| 5 | electrode array |
| 10 | lead paddle |
| 10a | upper side |
| 10b | contact side |
| 10c | proximal end |
| 11 | lead paddle body |
| 12 | guiding channel |
| 14 | outer edge region |
| 16 | longitudinal edge |
| 17 | tip end |
| 18 | electrodes |
| 20 | lead body |
| 20a | connection portion |
| 22 | anchoring sleeves |
| 24 | pins |
| 100 | neuromodulation system |
| 200 | spinal column |
| 210 | spinal cord |
| d | offset |
| D | distal end |
| E | distance between outermost edges of the electrode array (width) |
| F | distance between outermost edges of the electrode array (length) |
| G | gap |
| H | distance H between the right outermost edges of two neighboring electrodes in section S1 |
| I | distance between proximal edge of section S1 |
| J | distance between proximal edge from R1 to R2 |
| K | distance from longitudinal right edge of electrode in C2 to right outer longitudinal edge of the lead paddle |
| L | longitudinal direction |
| P | proximal end |
| R | radial direction |
| l | length of electrode |
| w | width of electrode |
| l1 | length of electrode array |
| w1 | width of electrode array |
| l2 | length of gap |
| C01 | column in first electrode section |
| C02 | column in first electrode section |
| C03 | column in first electrode section |
| C04 | Column in first electrode section |
| R0 | row in first electrode section |
| C1 | column in second electrode section |
| C2 | column in second electrode section |
| C3 | column in second electrode section |
| R1 | row in second electrode section |
| R2 | row in second electrode section |
| R3 | row in second electrode section |
| R4 | row in second electrode section |
| R5 | row in second electrode section |
| R6 | row in second electrode section |
| R7 | row in second electrode section |
| R8 | row in second electrode section |
| S1 | first electrode section |
| S2 | second electrode section |

The invention claimed is:

1. An electrode array for neuromodulation, the array defined by a longitudinal axis and a radial axis perpendicular to the longitudinal axis, the array consisting essentially of:
a first electrode section with more than two electrodes arranged in parallel along a common axis parallel to the longitudinal axis and densely packed in the first electrode section, wherein
the first electrode section comprises at least three columns aligned with the longitudinal axis and only one radial row along the radial axis; and a second electrode section with more electrodes than the first electrode section, the electrodes in the second electrode section arranged symmetrically with respect to the longitudinal axis, and with a transversal offset relative to each other; wherein
the first electrode section and the second electrode section are separated by a gap having a length in a range of 100-160% of a length of an electrode of the first or second electrode sections; and
the electrodes in the first electrode section are spaced apart from adjacent electrodes by a distance that is less than a distance between adjacent electrodes of the second electrode section.

2. The electrode array according to claim 1, wherein the first electrode section is arranged at a proximal end of the electrode array and/or the second electrode section is arranged at a distal end of the electrode array.

3. The electrode array according to claim 1, wherein the electrodes in the first electrode section are identical to the electrodes in the second electrode section.

4. The electrode array according to claim 3, wherein at least one electrode has a length that is 2.0-4.0 times of a width.

5. The electrode array according to claim 3, wherein all electrodes of the first and second electrode sections have a common orientation, the common orientation parallel to the longitudinal axis.

6. The electrode array according to claim 1, wherein the electrode array has a length that is of 8-14 times of a length of an electrode of the first or second electrode sections.

7. The electrode array according to claim 1, wherein the first electrode section is symmetrical with respect to the longitudinal axis and with respect to the radial axis in the first electrode section, and wherein the second electrode section is symmetrical with respect to the longitudinal axis and asymmetrical with respect to the radial axis in the section electrode section.

8. The electrode array according to claim 7, wherein the second electrode section comprises at least three columns aligned with the longitudinal axis and more than five radial rows.

9. The electrode array according to claim 1, wherein a distance between electrodes of the first electrode section is less than a width of an electrode of the first or second electrode sections, the distance chosen in a range of 50% to 95% of the width of the electrode of the first or second electrode sections.

10. The electrode array according to claim 1, wherein in the second electrode section, the electrodes in neighboring columns are arranged with a transversal offset relative to each other.

11. The electrode array according to claim 10, wherein in the second electrode section, a distance between neighboring electrodes arranged in a common column is in a range of 135% to 155% of the length of the electrode.

12. The electrode array according to claim 1, wherein a total number of electrodes in the electrode array is 16 electrodes.

13. The electrode array according to claim 1, wherein the more than two electrodes of the first electrode section are arranged in columns along the longitudinal axis, and the electrodes of the second electrode section are arranged in a number of columns less than the columns of the first electrode section.

14. The system of claim 13, wherein a portion of the electrodes of the second electrode section are positioned on the longitudinal axis of the electrode array.

15. A lead paddle comprising at least one electrode array, the at least one electrode array defined by a longitudinal axis and a radial axis perpendicular to the longitudinal axis, the at least one electrode array consisting essentially of:
a first electrode section with a first number of electrodes arranged in parallel columns, wherein the first electrode section comprises at least three columns aligned with the longitudinal axis and only one radial row along the radial axis; and
a second electrode section with a second number of electrodes, more than the first number, arranged symmetrically with respect to the longitudinal axis, and with a transversal offset relative to each other, wherein the second number of electrodes are arranged in a number of columns less than the parallel columns of the first electrode section.

16. A neuromodulation system comprising:
at least one lead paddle; and
at least one electrode array defined by a longitudinal axis and a radial axis perpendicular to the longitudinal axis, the at least one electrode array consisting essentially of:
a first electrode section with a first number of electrodes arranged in parallel, wherein:
the first electrode section comprises at least three columns aligned with the longitudinal axis and only one radial row along the radial axis; and
a second electrode section with a second number of electrodes, more than the first number, arranged symmetrically with respect to the longitudinal axis, and with a transversal offset relative to each other, wherein a portion of the second number of electrodes lies on the longitudinal axis.

17. The system of claim 16, wherein electrodes of the first and second electrode sections have a common orientation, parallel to the longitudinal axis of the electrode array.

18. The system of claim 17, wherein the width and length of the electrodes of the first electrode section are identical to the width and length of the electrodes of the second electrode section.

19. The system of claim 18, wherein the second number of electrodes of the second electrode section are arranged in parallel columns, the electrodes in neighboring columns arranged with a transversal offset relative to each other.

20. The system of claim 18, wherein a distance between the electrodes of the first electrode section is less than the width of the electrode.

* * * * *